US009938206B2

United States Patent
Weber et al.

(10) Patent No.: US 9,938,206 B2
(45) Date of Patent: Apr. 10, 2018

(54) HIGHLY BRANCHED HYDROCARBON ISOMERIZATION FOR AN AROMATIZATION REACTION

(71) Applicant: Chevron Phillips Chemical Company LP, The Woodlands, TX (US)

(72) Inventors: Eric P. Weber, Kingwood, TX (US); Tin-Tack Peter Cheung, Houston, TX (US); Yu Su, Houston, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 15/725,962

(22) Filed: Oct. 5, 2017

(65) Prior Publication Data

US 2018/0044263 A1    Feb. 15, 2018

Related U.S. Application Data

(63) Continuation of application No. 15/188,567, filed on Jun. 21, 2016, now Pat. No. 9,809,510.

(51) Int. Cl.
    *C07C 5/27*    (2006.01)
    *C07C 5/32*    (2006.01)
    (Continued)

(52) U.S. Cl.
    CPC ......... *C07C 5/2775* (2013.01); *B01J 29/7415* (2013.01); *C07C 5/41* (2013.01); *C07C 2529/74* (2013.01)

(58) Field of Classification Search
    CPC .................................. C07C 5/27; C07C 5/32
    (Continued)

(56) References Cited

U.S. PATENT DOCUMENTS

| 2,880,252 A * | 3/1959 | Raley ........................ C07C 5/44 |
| | | 585/414 |
| 5,401,365 A | 3/1995 | Chen et al. |

(Continued)

OTHER PUBLICATIONS

Barrera A., et al., "Isomerization of n-hexane over mono- and bimetallic Pd—Pt catalysts supported on $ZrO_2$—$Al_2O_3$ —$WO_x$ prepared by sol—gel," Applied Catalysis A: General, 2005, pp. 97-109, vol. 290, Elsevier B.V.
(Continued)

*Primary Examiner* — Thuan D Dang
(74) *Attorney, Agent, or Firm* — Conley Rose, P.C.; Rodney B. Carroll; Monte R. Rhodes

(57) ABSTRACT

A process for aromatizing hydrocarbons comprises: converting at least a portion of highly branched hydrocarbons in a feed stream into selectively convertible components, and aromatizing the selectively convertible components to produce an aromatization reactor effluent. The aromatization reactor effluent comprises an aromatic product. Converting at least the portion of the highly branched hydrocarbons into the selectively convertible components may include contacting the feed stream with an isomerization catalyst in an isomerization reaction system under isomerization reaction conditions; and isomerizing the portion of the highly branched hydrocarbons in the feed stream into the selectively convertible components.

16 Claims, 5 Drawing Sheets

(51) Int. Cl.
*B01J 29/74* (2006.01)
*C07C 5/41* (2006.01)

(58) Field of Classification Search
USPC .................. 585/322, 319, 739, 734, 407
See application file for complete search history.

(56) References Cited

U.S. PATENT DOCUMENTS

| | | | |
|---|---|---|---|
| 5,877,367 | A | 3/1999 | Witte |
| 6,812,180 | B2 | 11/2004 | Fukunaga |
| 7,153,801 | B2 | 12/2006 | Wu |
| 9,200,214 | B2 | 12/2015 | Cheung |
| 9,809,510 | B1 | 11/2017 | Weber et al. |

OTHER PUBLICATIONS

Boskovic, G., et al., "n-Hexane isomerization over Pt—Na(H)Y catalysts obtained by different preparation methods," Catalysis Today, 2001, pp. 123-128, vol. 65, Elsevier Science B.V.

Brito, K. D., et al., "Kinetic Modelling of the Isomerization of n-Hexane Using Bifunctional Pt-Ni/MOR Catalysts," http://www.portalabpg.org.br/bjpg, Brazilian Journal of Petroleum and Gas, 2008, pp. 1-8, vol. 2, No. 1.

Buchholz, Thomas, et al., "Hydroisomerization of n-hexane over Pt/sulfated zirconia: activity, reversible deactivation, and surface analysis," Applied Catalysis A: General, 1999, pp. 225-236, vol. 189, Elsevier Science B.V.

Campelo, J. M., et al., "Comparison of the activity and selectivity of Pt/SAPO-5 and Pt/SAPO-11 in n-hexane and n-heptane hydroconversion," Applied Catalysis A: General, 1997, pp. 53-62, vol. 152, Elsevier Science B.V.

Chaudhari, K., et al., "Mesoporous Aluminosilicate of the MCM-41 Type: Its Catalytic Activity in n-Hexane Isomerization," 1999, pp. 81-90, vol. 186, Academic Press.

Chica, A., et al., "Isomerization of $C_5$—$C_7$ n-alkanes on unidirectional large pore zeolites: activity, selectivity and adsorption features," Catalysis Today, 2001, pp. 101-110, vol. 65, Elsevier Science B.V.

Chu, Hon Yue, et al., "Skeletal Isomerization of Hexane over Pt/H-Beta Zeolites: Is the Classical Mechanism Correct?" Journal of Catalysis, 1998, pp. 352-362, vol. 178, Academic Press.

Das, Tapan KR., et al., "Hydroisomerization of n-hexane over Pt-ETS-10," Catalysis Letters, 1997, pp. 113-117, vol. 44, J.C. Baltzer AG, Science Publishers.

Essayem, N., et al., "Heteropolyacid Catalysts for Hydroisomerization of n-Hexane: Effects of Alkali Salt Modification," Journal of Catalysis, 2001, pp. 157-162, vol. 204, Academic Press.

Fraissard, Jacques, et al., "Isomerization of hexane on PtAu nanoparticles supported on zeolites," Catalysis Today, 2007, pp. 338-340, vol. 122, Elsevier B.V.

Ivanov, A. V., et al., "Isomerization of n-hexane on the Pt-promoted Keggin and Dawson tungstophosphoric heteropoly acids supported on zirconia," Applied Catalysis A: General, 2004, pp. 65-72, vol. 259, Elsevier B.V.

Jordão, Maura H., "Zeolite supported Pt-Ni catalysts in n-hexane isomerization," Applied Catalysis A: General, 2007, pp. 1-6, vol. 319, Elsevier B.V.

Lee, Jeong-Kyu, et al., "Characteristics of Pt/H-beta and Pt/H-mordenite catalysts for the isomerization of n-hexane," Catalysis Today, 1997, pp. 235-242, vol. 38, Elsevier Science B.V.

Lee, Jeong-Kyu, et al., "Sulfur Tolerance of Zeolite Beta-Supported Pd-Pt Catalysts for the Isomerization of n-Hexane," Journal of Catalysis, 1998, pp. 208-216, vol. 177, Academic Press.

Lima, Patrícia M., et al., "Isomerization of n-hexane on Pt-Ni catalysts supported on nanocrystalline H-BEA zeolite," Catalysis Today, 2011, 8 pages, Elsevier B.V.

Maldonado, F. J., et al., "Influence of the Alkali in Pt/Alkali-β Zeolite on the Pt Characteristics and Catalytic Activity in the Transformation of n-Hexane," Journal of Catalysis, 2000, pp. 342-351, vol. 195, Academic Press.

Ravishankar, R., et al., "Hydroisomerization of n-hexane over Pt-H-MCM-22," Applied Catalysis A: General, 1996, pp. 47-59, vol. 142, Elsevier Science B.V.

Ridgway, Jr., J. A., et al., "Hexane Isomer Equilibrium," Industrial and Engineering Chemistry, Sep. 1959, pp. 1023-1026, vol. 51, No. 9.

Santiesteban, J. G., et al., "The Role of Platinum in Hexane Isomerization over $Pt/FeO_y/WO_x/ZrO_2$," Journal of Catalysis, 2001, pp. 25-33, vol. 202, Academic Press.

Saxena, Sandeep K., et al., "Effect of acid treatments on physico-chemical properties and isomerization activity of mordenite," Catalysis Today, 2009, pp. 215-219, vol. 141, Elsevier B.V.

Siffert, Stéphane, et al., "Influence of Acidity-Basicity in 13C-Labeled Hexane Isomerization Reactions on Exchanged Pt-β Zeolite: Mechanistic Studies," Journal of Catalysis, 1999, pp. 19-28, vol. 184, Academic Press.

Sinha, A. K., et al., "Hydroisomerization of n-hexane over Pt-SAPO-11 and Pt-SAPO-31 molecular sieves," catalysis Today, 1999, pp. 293-302, vol. 49, Elsevier Science B.V.

Song, Yue-Qin, et al., "Effect of variations in pore structure and acidity of alkali treated ZSM-5 on the isomerization performance," Journal of Molecular Catalysis A: Chemical, 2009, pp. 130-137, vol. 310, Elsevier B.V.

Van De Runstraat, A., et al., "Kinetics of Hydro-isomerization of n-Hexane over Platinum Containing Zeolites," Journal of Catalysis, 1997, pp. 77-84, vol. 171, Academic Press.

Vaudagna, S. R., et al., "$SO_4^{2-}$—$ZrO_2$ and $Pt/SO_4^{2-}$—$ZrO_2$: Activity and Stability during n-Hexane Isomerization," Journal of Catalysis, 1997, pp. 389-393, vol. 169, Academic Press.

Viswanadham, N., et al., "Effect of acidity and porosity changes of dealuminated mordenites on n-hexane isomerization," Journal of Molecular Catalysis A: Chemical, 2006, pp. 15-21, vol. 258, Elsevier B.V.

Vu, T. N., et al., "Platinum-tungstated zirconia isomerization catalysts Part II. Effect of platinum and tungsten loading on the mechanism of isomerization of n-hexane: a kinetic study," Journal of Catalysis, 2005, pp. 468-479, vol. 231, Elsevier Inc.

Yashima, T., et al., "Isomerization of n-hexane over Platinum loaded zeolite catalysts," Catalysis Today, 1996, pp. 279-283, vol. 29, Elsevier Science B.V.

Yoshioka, Carlos M. N., et al., "n-Hexane isomerization on Ni-Pt catalysts/supported on HUSY zeolite: The influence from a metal content," Catalysis Today, 2005, pp. 693-698, vol. 107-108, Elsevier B.V.

* cited by examiner

HIGHLY BRANCHED HYDROCARBON ISOMERIZATION FOR AN AROMATIZATION REACTION

CROSS-REFERENCE TO RELATED APPLICATIONS

This application is a continuation of and claims priority to U.S. patent application Ser. No. 15/188,567 filed Jun. 21, 2016, and entitled "Highly Branched Hydrocarbon Isomerization for an Aromatization Reaction," which is incorporated by reference herein in its entirety.

FIELD

This disclosure relates generally to a system and method for continually operating an aromatization process. More particularly, the disclosure relates to continually operating an aromatization process while converting highly branched hydrocarbons within the system to convertible components.

BACKGROUND

Typical aromatization processes may be carried out using a variety of reactors containing dehydrocyclization catalysts. The aromatization process encompasses a number of reactions, which are typically carried out in the presence of a catalyst, such as dehydrocyclization, hydrodecyclization, isomerization, hydrogenation, dehydrogenation, hydrocracking, cracking, or combinations thereof. Aromatization reactions are intended to convert paraffins, naphthenes, and olefins to aromatics and hydrogen.

The feed stream may comprise components that may be difficult to convert in the aromatization process. These components may build up in recycle loops and are typically removed through separation within the system. Alternatively, an upstream process may be used to reduce the amount of non-convertible components in the feed stream.

SUMMARY

An aspect of the disclosure includes a process for aromatizing hydrocarbons that comprises converting at least a portion of highly branched hydrocarbons in a feed stream into selectively convertible components, and aromatizing the selectively convertible components in an aromatization reaction zone to produce an aromatization reactor effluent. The aromatization reactor effluent comprises an aromatic product. Converting at least the portion of the highly branched hydrocarbons into the selectively convertible components may include contacting the feed stream with an isomerization catalyst contained within an isomerization reactor in an isomerization reactor system under isomerization reaction conditions; and isomerizing the portion of the highly branched hydrocarbons in the feed stream into the selectively convertible components. The isomerization catalyst may comprise a β zeolite. The isomerization catalyst may comprise a Group 10 metal, and/or the isomerization catalyst may comprise between about 0.1 wt. % and about 1 wt. % platinum on the β zeolite. A silicon to aluminum molar ratio of the β zeolite may be between about 20 to about 60.

The highly branched hydrocarbons may comprise hydrocarbons having six or seven carbon atoms with an internal quaternary carbon or hydrocarbons having six carbons atoms and two adjacent internal tertiary carbons or mixtures thereof. The highly branched hydrocarbons may comprise dimethylbutanes, trimethylbutanes, dimethylpentanes, or mixtures thereof. The highly branched hydrocarbons with six or seven carbon atoms with an internal quaternary carbon may comprise, for example, 2,2-dimethylbutane, 2,2-dimethylpentane, 3,3-dimethylpentane, 2,2,3-trimethylbutane, or mixtures thereof. The highly branched hydrocarbons with six carbon atoms and an adjacent internal tertiary carbons may comprise 2,3-dimethylbutane. The highly branched hydrocarbons do not easily convert to aromatic products and instead tend to convert to light hydrocarbons.

The selectively convertible components may comprise hydrocarbons having six or seven carbon atoms without an internal quaternary carbon or hydrocarbons having six carbon atoms without two adjacent internal tertiary carbons, or mixtures thereof. The selectively convertible components may comprise methylpentanes, methylhexanes, dimethylpentanes or mixtures thereof, and/or the selectively convertible components may comprise at least one of 2-methylpentane, 3-methylpentane, 2,4-dimethylpentane, 2,3-dimethylpentane, n-hexane, 2-methylhexane, 3-methylhexane, n-heptane, or mixtures thereof. The feed stream may comprise between about 0.1 wt. % and about 100 wt. % highly branched hydrocarbons. The selectively convertible components readily convert to aromatic products without production of light hydrocarbons.

Aromatizing the selectively convertible components may comprise contacting the selectively convertible components with a dehydrocyclization catalyst in an aromatization reaction zone under aromatization reaction conditions, and converting the selectively convertible components into one or more aromatics in the aromatic product. The dehydrocyclization catalyst may comprise at least one Group VIII metal and zeolitic support. The least one Group VIII metal may comprise platinum and the zeolitic support comprises silica bound L-zeolite. The dehydrocyclization catalyst may comprise one or more halogens. The aromatization reactor effluent may comprise the highly branched hydrocarbons, and the process may also include: separating at least a portion of the aromatic product from the aromatization reactor effluent to obtain a raffinate stream, where the raffinate stream has an increased highly branched hydrocarbon concentration compared to the aromatization reactor effluent; and providing the raffinate stream to the isomerization reactor system as the feed stream. The aromatization reactor effluent may comprise the highly branched hydrocarbons, and the process may also include: separating at least a portion of the aromatic product from the aromatization reactor effluent to obtain a raffinate stream, where the raffinate stream has an increased highly branched hydrocarbon concentration compared to the aromatization reactor effluent; and separating the highly branched hydrocarbons from the raffinate stream to obtain the feed stream to the isomerization reactor system, where the feed stream has an increased highly branched hydrocarbon concentration compared to the lean raffinate stream. The aromatization reactor effluent may comprise the highly branched hydrocarbons, and the process may also include: separating at least a portion of the highly branched hydrocarbons from the aromatization reactor effluent to obtain a highly branched hydrocarbon stream, where the highly branched hydrocarbon stream has an increased highly branched hydrocarbon concentration compared to the aromatization reactor effluent; and providing the highly branched hydrocarbon stream to the isomerization reactor system as the feed stream.

In further aspects of the disclosure is a process for aromatizing hydrocarbons comprises recovering highly branched hydrocarbons in an aromatization reactor effluent produced in an aromatization reaction zone; converting at least a portion of the highly branched hydrocarbons into selectively convertible components; and aromatizing the selectively convertible components to produce an aromatic product. The process may also include feeding the selectively convertible components to an inlet of an aromatization reactor system, where the aromatization reactor system produces the aromatization reactor effluent wherein the aromatization reactor system comprises at least one aromatization reactor and at least one furnaces located upstream of each reactor to heat the streams prior to entering an aromatization reactor in the aromatization reactor system. Converting at least the portion of the highly branched hydrocarbons may comprise contacting the highly branched hydrocarbons with an isomerization catalyst in at least one isomerization reactor within an isomerization reactor system, and isomerizing at least the portion of the highly branched hydrocarbons into the selectively convertible components. The isomerization catalyst may comprise a β zeolite and a Group 10 metal. The selectively convertible components may comprise at least one of 2-methylpentane, 3-methylpentane, 2,4-dimethylpentane, 2,3-dimethylpentane, n-hexane, 2-methylhexane, 3-methylhexane, n-heptane, or mixtures thereof.

In some aspects, a process for aromatizing hydrocarbons comprises: concentrating highly branched hydrocarbons in a hydrocarbon stream to yield a highly branched hydrocarbon rich stream, converting at least a portion of the highly branched hydrocarbons in the highly branched hydrocarbon rich stream into selectively convertible components, and aromatizing the selectively convertible components in an aromatization reactor system to produce an aromatization reactor effluent comprising an aromatic product. Concentrating the highly branched hydrocarbons may comprise separating aromatics from the hydrocarbon stream to yield the highly branched hydrocarbons rich stream. Concentrating the highly branched hydrocarbons may also comprise separating at least a portion of the highly branched hydrocarbons from the hydrocarbon stream to yield the highly branched hydrocarbons rich stream. The hydrocarbon stream may be an aromatization reactor effluent. Converting at least the portion of the highly branched hydrocarbons into selectively convertible components may comprise contacting the highly branched hydrocarbons with an isomerization catalyst, and isomerizing at least the portion of the highly branched hydrocarbons into the selectively convertible components. The isomerization catalyst may comprise a β zeolite and platinum.

In various aspects, an aromatization reactor system comprises at least one aromatization reactor comprising a dehydrocyclization catalyst, a feed inlet, and an aromatization reactor effluent outlet; a separator in fluid communication with the aromatization reactor effluent outlet, and an isomerization reactor system comprising an isomerization catalyst contained within at least one isomerization reactor. The separator is configured to separate at least a portion of an aromatization reactor effluent stream comprising an aromatic product and highly branched hydrocarbons into an aromatic product stream enriched in aromatics and a highly branched hydrocarbon stream enriched in the highly branched hydrocarbons. The separator is also configured to pass the highly branched hydrocarbon stream out of a highly branched hydrocarbon stream outlet, and the isomerization reactor system is in fluid communication with the highly branched hydrocarbon stream outlet to receive the highly branched hydrocarbon stream. The isomerization reactor system is configured to isomerize at least a portion of the highly branched hydrocarbons in the highly branched hydrocarbon stream into selectively convertible components, and an outlet of the isomerization reactor system is in fluid communication with the feed inlet of the aromatization reactor system to pass at least a portion of the selectively convertible components from the isomerization reactor system to the aromatization reaction zone. The isomerization catalyst may comprise a β zeolite, and a silicon to aluminum molar ratio of the β zeolite may be between about 20 to about 60. The isomerization catalyst may comprise a Group 10 metal. The isomerization catalyst may comprise between about 0.1 wt. % and about 1 wt. % platinum on the β zeolite. The dehydrocyclization catalyst may comprise at least one Group VIII metal and zeolitic support. The least one Group VIII metal may comprise platinum and the zeolitic support comprises silica bound L-zeolite, and/or the dehydrocyclization catalyst comprises one or more halogens.

These and other features will be more clearly understood from the following detailed description taken in conjunction with the accompanying drawings and claims.

DETAILED DESCRIPTION

As is generally understood, an aromatization "reaction", typically takes place within an aromatization "reactor." The reactor(s) employed in this processes described herein may be any conventional type of reactor that maintains a catalyst within the reactor and may accommodate a continuous flow of hydrocarbon. The aromatization reactor systems described herein may comprise a fixed catalyst bed system, a moving catalyst bed system, a fluidized catalyst bed system, or combinations thereof. Suitable reactors may include, but are not limited to, fixed bed reactors including radial flow reactors, bubble bed reactors, or ebullient bed reactors. The flow of the feed stream may be upward, downward, or radially through the reactor. In various aspects, the aromatization reactor system described herein may be operated as a series of adiabatic reactors or an isothermal reactor system. As used herein, a "hydrocarbon stream" comprises hydrocarbons, though components other than molecules comprising hydrogen and carbon may be present in the stream (for example, hydrogen gas). In some aspects, a "hydrocarbon" may comprise individual molecules that comprise one or more atoms other than hydrogen and carbon (for example, nitrogen, oxygen, or mixtures thereof.).

Disclosed herein is a system and process for converting a hydrocarbon feed stream comprising branched components into an aromatic product. The feed stream may comprise various components that are difficult to convert to aromatic products. For example, dimethylbutanes (DMBs) may be difficult to convert to an aromatic product due to the high degree of branching. These highly branched compounds may generally build up in recycle loops if they are present so that these components must be separated and removed from the system. While some highly branched compounds are difficult to convert to aromatic products, the isomers of the branched compounds may be more easily converted. For example, the isomers of dimethylbutanes including 2-methyl pentane, 3-methyl pentane, and n-hexane are all capable of being converted in an aromatization process to aromatic products.

As disclosed herein, an isomerization process may be incorporated into the aromatization process. In this process, the highly branched hydrocarbons may be concentrated and passed to an isomerization reactor system. By operating at the appropriate conditions, the highly branched hydrocarbons may be isomerized into selectively convertible components. These selectively convertible components may then be passed to the aromatization process to convert the selectively convertible components into aromatic products.

Figure 1:
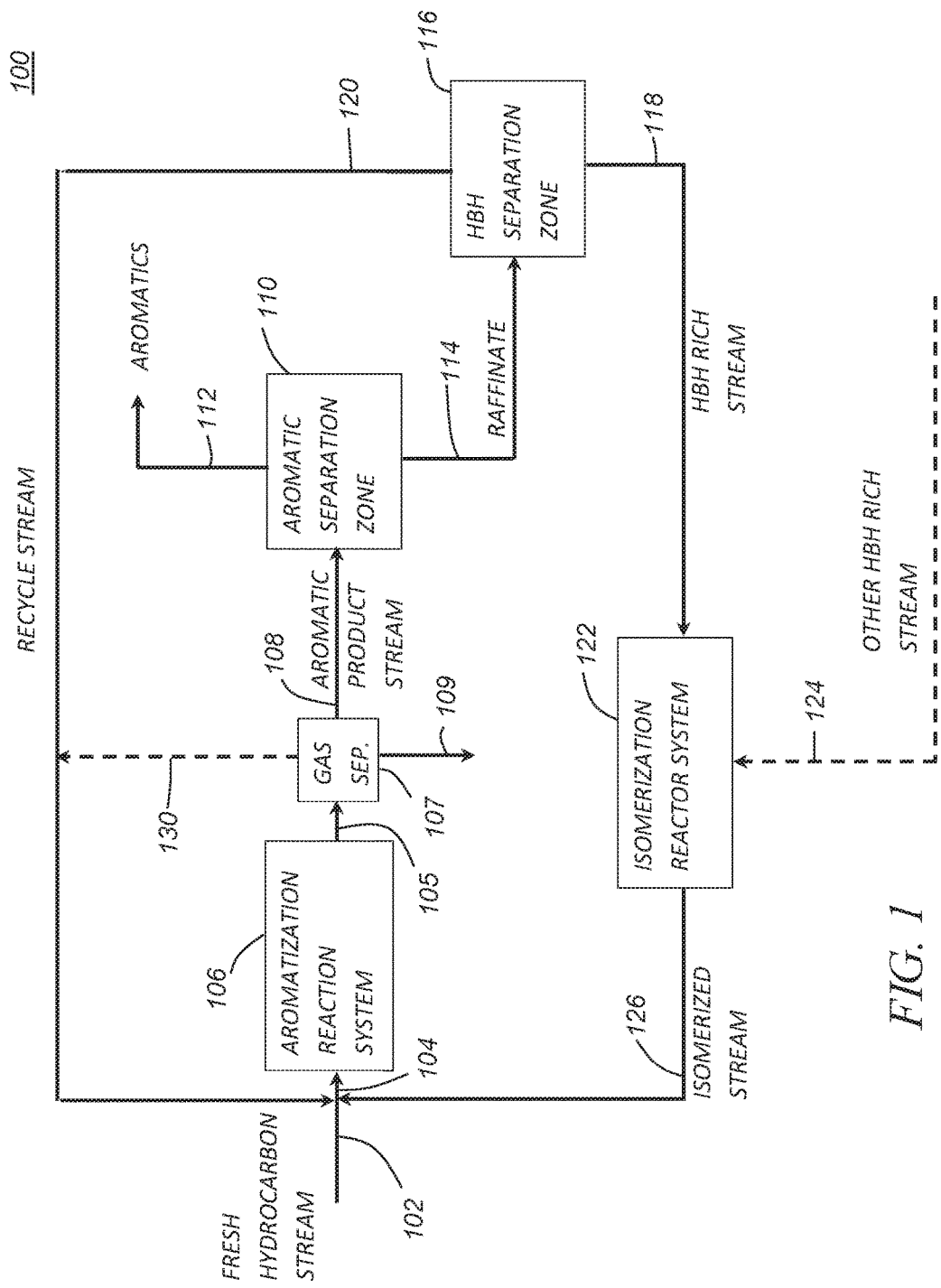
FIG. 1 is a schematic flow diagram of some aspects of an aromatization process of the disclosure.

An aromatization system 100 is shown in FIG. 1. At the inlet of the process, a fresh hydrocarbon stream comprising unreacted hydrocarbons is fed through line 102, which may be combined with one or more recycle streams in line 120 and one or more isomerized streams in line 126 before passing to the aromatization reactor system 106. Various feed streams may be suitable for use with aromatization processes, and the feed stream may comprise components that may be converted in the aromatization process and components that may not be readily converted to aromatic products. As used herein, the term "selectively convertible components" refers to hydrocarbon components that may be converted to aromatic products such as aromatic hydrocarbons within the aromatization reactor system 106. The selectively convertible components may not comprise an internal quaternary carbon, or hydrocarbons having six carbon atoms and two adjacent internal tertiary carbon atoms, or mixtures thereof.

The selectively convertible components may generally comprise non-aromatic hydrocarbons. The selectively convertible components in the feed stream to the aromatization system 100 comprising an aromatization reactor system 106 may comprise a mixture of hydrocarbons comprising $C_6$ to $C_7$ hydrocarbons containing up to about 10 wt % and alternatively up to about 15 wt % of $C_5$ and lighter hydrocarbons ($C_5^-$) and containing up to about 25 wt % of $C_8$ and heavier hydrocarbons ($C_8^+$). For example, the feed stream may include naphtha boiling range hydrocarbons comprising a majority of $C_6$-$C_7$ paraffins. In some aspects, the feed stream preferably is $C_6$ or higher non-aromatic organic compounds. Non-limiting examples of preferred $C_6$-$C_7$ paraffinic feed stream components include n-hexane, or n-heptane. The selectively convertible components may also comprise branched hydrocarbons including, but not limited to, methylpentanes (for example, 2-methylpentane, 3-methylpentane), methylhexanes (for example, 2-methylhexane, 3-methylhexane), and mixtures thereof.

Examples of suitable feed streams include straight-run naphthas from petroleum refining or fractions thereof that have been hydrotreated to remove sulfur and other catalyst poisons. Also suitable are synthetic naphthas or naphtha fractions derived from other sources such as coal, natural gas, or from processes such as Fischer-Tropsch processes, fluid catalytic crackers, and hydrocrackers. In various aspects, the naphtha feed stream may be derived directly from crude petroleum by distillation, or may be indirectly derived from a petroleum feed stream by separation of a naphtha boiling range stream from the effluent from hydrocracking, coking or catalytic cracking.

The feed stream may also comprise various highly branched hydrocarbons that may not be converted in the aromatization reactor system 106. These hydrocarbons may have boiling points close to the selectively convertible components in the feed stream and be present in the feed stream as a result of upstream processing. For example, dimethylbutanes boil near n-hexane, and also near methylpentanes, both of which may be used as feed streams for the aromatization reactor system 106. In some aspects, the feed stream comprises a highly branched hydrocarbon that is not readily converted to an aromatic compound in the aromatization reactor system 106. As used herein a "highly branched hydrocarbons" refer to hydrocarbons having six or seven carbon atoms with at least one internal quaternary carbon, or hydrocarbons having six carbon atoms and at least two adjacent internal tertiary carbon atoms, or mixtures thereof regardless of total molecular weight or carbon atom content. The highly branched hydrocarbons may include, but are not limited to, dimethylbutanes (for example, 2,2-dimethylbutane, 2,3-dimethylbutane), dimethylpentanes (for example, 2,2-dimethylpentane, 3,3-dimethylpentane), trimethylbutanes (for example, 2,2,3-trimethylbutane) and mixtures thereof.

The amount of highly branched hydrocarbons in the fresh hydrocarbon stream 102 to the aromatization system 100 may vary based on the source of the feed stream. In some aspects, the net unreacted hydrocarbon in the feed stream to the process may contain from about 0.1 wt. % to about 20 wt. %, from about 0.3 wt. % to about 18 wt. %, or from about 0.5 wt. % to about 15 wt. % highly branched hydrocarbons, based on weight of the net or unreacted hydrocarbon in the feed stream to the process. The term "unreacted hydrocarbon" is used herein refers to the net hydrocarbon in the feed stream to the process which has not been passed through the aromatization reactor system 106. While described as having an upper limit, the composition of the feed stream, including the unreacted hydrocarbon, may have higher amounts of highly branched hydrocarbons, where the isomerization reactor system may convert the highly branched hydrocarbons into selectively convertible components. As a result, the feed stream, which may include the unreacted hydrocarbon, may comprise between about 0.1 wt. % and about 100 wt. % of the highly branched hydrocarbons, where the highly branched hydrocarbons may be converted into selectively convertible components within the aromatization system 100.

While not shown in FIG. 1, various upstream hydrocarbon pretreatment steps may be used to prepare the hydrocarbon for the aromatization process. For example, hydrotreating may be used to remove catalyst poisons such as sulfur. Contacting the hydrocarbon with a nickel catalyst, for example, prior to the aromatization reaction may also protect against failure of the hydrotreating system. In various aspects, the hydrocarbon stream may have a sulfur content ranging from less than 200 ppbw, alternatively less than 100 ppbw, alternatively from about 10 parts per billion by weight (ppbw) to about 100 ppbw.

The fresh hydrocarbon stream passing through line 102 may be combined with one or more recycle streams in line 120 and one or more isomerized streams in line 126. These streams (120, 126 or both) may contain hydrogen, unreacted selectively convertible components, and/or highly branched hydrocarbons that have been isomerized into selectively convertible components. The combined feed stream passing through line 104 may then pass to the aromatization reactor system 106. Various equipment may be used to modify or adjust the conditions of the streams prior to entering the aromatization reactor system 106 such as heat exchangers, pumps, treating units (for example, sulfur removal systems), and the like.

The aromatization reactor system 106 may comprise one or more reactors to contact the selectively convertible components in the feed stream with a dehydrocyclization catalyst under aromatization reaction conditions to form aromatic components. As the aromatization reaction is generally endothermic, the combined feed stream in line 104 may be heated in one or more furnaces prior to introduction to each of the one or more aromatization reactors. The one or more furnaces and one or more aromatization reactors are not shown as separate features of the aromatization reactor system 106.

In some aspects, the aromatization reactor system 106 may comprise a plurality of reactors arranged in series. Heaters such as furnaces may be located upstream of each reactor to heat the streams prior to entering an aromatization reactor in the aromatization reactor system. The furnaces may comprise any type of furnace capable of raising the temperature of the reactant stream to achieve the desired inlet temperature to the subsequent reactor. The temperature may be raised so that the aromatization reactions proceed in the subsequent reactors, which is generally needed due to the endothermic nature of the aromatization process. The aromatization reactor system 106 may comprises three or more serially connected reactors, and all of the reactors may be the same or different in size or configuration. In various aspects, all of the reactors may be radial flow reactors with the hydrocarbon stream passing through the reactors in inward or outward flow. In some aspects, the reactors may be sized according to known techniques, and all of the reactors may be the same size. Alternatively, one or more reactors may be different sizes.

In general, the aromatization reactions occur under process conditions that thermodynamically favor the aromatization reactions and limit undesirable hydrocracking reactions. The aromatization reaction may be carried out using any conventional aromatization conditions, and may be carried out at reactor inlet temperatures ranging from about 600° F. to about 1100° F., alternatively from about 650° F. to about 1100° F., alternatively from about 700° F. to about 1100° F., alternatively from about 800° F. to about 1050° F., alternatively from about 850° F. to about 1050° F. Reaction pressures may range from about atmospheric pressure to about 500 psig, alternatively from about 25 psig to about 300 psig, and alternatively from about 30 psig to about 100 psig. The molar ratio of hydrogen to hydrocarbon in the combined feed stream 104 is normally between about 0.1 and about 10, alternatively from about 0.5 to about 5.0, and alternatively from about 1:1 to about 3:1. The liquid hourly space velocity (LHSV) for the feed stream over the dehydrocyclization catalyst is from about 0.5 hr$^{-1}$ to about 20 hr$^{-1}$, and alternatively from about 0.50 hr$^{-1}$ to about 5.0 hr$^{-1}$ based on the catalyst in the aromatization reactor system 106.

In various aspects, the aromatization reactors in the aromatization reactor system 106 may each contain a dehydrocyclization catalyst for carrying out an aromatization process. As is known to those of ordinary skill in the art, a suitable dehydrocyclization catalyst is capable of converting at least a portion of aliphatic and/or naphthenic hydrocarbons (for example, non-aromatic hydrocarbons) in a hydrocarbon stream to aromatic hydrocarbons. Any catalyst capable of carrying out an aromatization reaction may be used alone or in combination with additional catalytic materials in the reactors. Suitable catalysts may include acidic or non-acidic catalysts. In some aspects, the catalyst is a non-acidic catalyst. A suitable non-acidic catalyst may comprise a non-acidic zeolite support, at least one group VIII metal, and one or more halides. Suitable halides include chloride, fluoride, bromide, iodide, or combinations thereof. Suitable Group VIII metals include iron, cobalt, nickel, ruthenium, rhodium, palladium, osmium, iridium, platinum, or combinations thereof. Examples of catalysts suitable for use with the aromatization reactor system described herein are AROMAX® catalysts available from the Chevron Phillips Chemical Company LP of The Woodlands, Tex., and those discussed in U.S. Pat. No. 6,812,180 to Fukunaga entitled "Method for Preparing Catalyst" and U.S. Pat. No. 7,153,801 to Wu entitled "Aromatization Catalyst and Methods of Making and Using Same," each of which is incorporated herein by reference as if reproduced in their entirety.

The supports for catalysts may generally include any inorganic oxide. These inorganic oxides may include bound large pore aluminosilicates (zeolites), amorphous inorganic oxides and mixtures thereof. Large pore aluminosilicates may include, but are not limited to, L-zeolite, Y-zeolite, mordenite, omega zeolite, beta zeolite, and the like. Amorphous inorganic oxides may include, but are not limited to, aluminum oxide, silicon oxide, and titania. Suitable bonding agents for the inorganic oxides may include, but are not limited to, silica, alumina, clays, titania, and magnesium oxide.

Zeolite materials, both natural and synthetic, are known to have catalytic properties for many hydrocarbon processes. Zeolites typically are ordered porous crystalline aluminosilicates having structure with cavities and channels interconnected by channels. The cavities and channels throughout the crystalline material generally may be of a size to allow selective separation of hydrocarbons.

The term "zeolite" generally refers to a particular group of hydrated, crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms may be equal to about 2. The framework exhibits a negative electrovalence that typically is balanced by the inclusion of cations within the crystal such as metals, alkali metals, alkaline earth metals, or hydrogen.

L-type zeolite catalysts are a sub-group of zeolitic catalysts. Typical L-type zeolites contain mole ratios of oxides in accordance with the following formula:

$$M2/nO.Al_2O_3.xSiO_2.yH_2O$$

wherein "M" designates at least one exchangeable cation such as barium, calcium, cerium, lithium, magnesium, potassium, sodium, strontium, and zinc as well as non-metallic cations like hydronium and ammonium ions which may be replaced by other exchangeable cations without causing a substantial alteration of the basic crystal structure of the L-type zeolite. The "n" in the formula represents the valence of "M", "x" is 2 or greater; and "y" is the number of water molecules contained in the channels or interconnected voids with the zeolite. Bound potassium L-type zeolites, or KL zeolites, have been found to be particularly desirable. The term "KL zeolite" as used herein refers to L-type zeolites in which the principal cation M incorporated in the zeolite is potassium. A KL zeolite may be cation-exchanged or impregnated with another metal and one or more halides to produce a platinum-impregnated, halided zeolite or a KL supported Pt-halide zeolite catalyst.

In various aspects, the at least one Group VIII metal is platinum. In other aspects, the at least one Group VIII metal is platinum and gold. In still further aspects, the at least one Group VIII metal is platinum and rhenium. The platinum and optionally one or more halides may be added to the zeolite support by any suitable method, for example via impregnation with a solution of a platinum-containing compound and one or more halide-containing compounds. For example, the platinum-containing compound may be any decomposable platinum-containing compound. Examples of such compounds include, but are not limited to, ammonium tetrachloroplatinate, chloroplatinic acid, diammineplatinum (II) nitrite, bis-(ethylenediamine)platinum (II) chloride, platinum (II) acetylacetonate, dichlorodiammine platinum, platinum (II) chloride, tetraammineplatinum (II) hydroxide, tetraammineplatinum chloride, and tetraammineplatinum (II) nitrate.

In some aspects, the catalyst is a zeolitic support with a platinum-containing compound and at least one ammonium halide compound. The ammonium halide compound may comprise one or more compounds represented by the formula $N(R)_4X$, where X is a halide and where R represents a hydrogen or a substituted or unsubstituted carbon chain molecule having 1-20 carbons wherein each R may be the same or different. In various aspects, R is selected from the group consisting of methyl, ethyl, propyl, butyl, and combinations thereof, more specifically methyl. Examples of suitable ammonium compounds are represented by the formula $N(R)_4X$ include ammonium chloride, ammonium fluoride, and tetraalkylammonium halides such as tetramethylammonium chloride, tetramethylammonium fluoride, tetraethylammonium chloride, tetraethylammonium fluoride, tetrapropylammonium chloride, tetrapropylammonium fluoride, tetrabutylammonium chloride, tetrabutylammonium fluoride, methyltriethylammonium chloride, methyltriethylammonium fluoride, and combinations thereof.

The catalyst may be employed in any of the conventional types or structures known to the art. It may be employed in the form of extrudates, pills, pellets, granules, broken fragments, or various special shapes, disposed within the aromatization reactor system 106 (for example, in a fixed bed), and the charging stock may be passed therethrough in the liquid, vapor, or mixed phase, and in either upward or downward, or inward or outward flow.

The selectivity for converting the selectively convertible components to aromatics is a measure of the effectiveness of the aromatization reaction in converting selectively convertible components to the desired and valuable products: aromatics and hydrogen, as opposed to the less desirable by-products, such as products from hydrocracking in the aromatization reactor system 106. The dehydrocyclization catalyst is used under reaction conditions effective to achieve per pass conversion of selectively convertible components to aromatics and other hydrocarbons of at least 50 wt. %, more preferably at least 60 wt. %, and most preferably at least 70 wt. %. The yield of desired aromatics product, on a per pass basis, is the per pass conversion times the selectivity. The term "selectivity" as used herein is defined as a percentage of moles of selectively convertible components converted to aromatics compared to moles converted to aromatics and other products (for example, cracked products). Thus, percent selectivity for selectively convertible components may be defined by the following formula: Selectivity=(100×moles of selectively convertible components converted to aromatics)/(moles of selectively convertible components converted to aromatics and other products). Isomerization of paraffins and interconversion paraffins and alkylcyclopentanes having the same number of carbon atoms per molecule are not considered in determining selectivity.

The aromatization product stream from the aromatization reactor system 106 may pass to a gas separation zone 107 through line 105, where gas such as hydrogen present in the aromatization product stream can be separated into one or more gaseous streams. The hydrogen separated in the gas separation zone 107 may be recycled to the aromatization reaction system 106 through line 130, which may be combined with another recycle line such as recycle line 120 and combined with the fresh hydrocarbon stream 102 upstream of the aromatization reactor system 106. A hydrogen product stream, line 109, can also be produced in the gas separation zone 107. The hydrogen product stream can pass out of the system 100, or be used for any other purposes within the system 100.

The remaining components from aromatization reaction zone 106, having passed through the gas separation zone 107, passes through line 108 to an aromatic separation zone 110, where the aromatic separation zone 110 may comprise a series of separation steps. Within the aromatic separation zone 110, a separation step may be carried out on the aromatic product to separate the aromatic hydrocarbons from the non-aromatic hydrocarbons. A product stream rich in aromatic material may be withdrawn through line 112 from the aromatic separation zone 110. The product stream rich in the aromatic material may leave the system and/or pass through one or more downstream treatment steps for further processing. In various aspects, the product stream rich in the aromatic material may comprise more than 80 wt. %, more than 90 wt. %, or more than 95 wt. % by weight aromatic components. The separated non-aromatic components may be withdrawn as a raffinate stream through line 114. The separation of the aromatics from the non-aromatics in the aromatics separation zone 110 may be done by any suitable separation process including, but not limited to, extraction using a solvent, distillation, and/or by the use of molecular sieves. In any of these separation processes, the term "raffinate" is used to refer to the paraffins rich stream separated from the aromatics product. In some aspects, the term "rich in paraffins" is used to mean more than 50 wt. % by weight paraffins, or alternatively, more than 80 wt. % paraffins.

The separation in the aromatics separation zone 110 may be carried out by extractive distillation to separate the "raffinate" stream, which is rich in non-aromatics, from the aromatization product stream in line 108.

In some aspects, the raffinate stream may be separated from the aromatics in the aromatics separation zone 110 with the aid of a solvent. In these aspects, the aromatics may be absorbed into a solvent and thereby extracted from the aromatic product stream as an aromatics rich stream. In other aspects, the aromatics are combined with a solvent and the aromatic-solvent azeotrope is separated by distillation as an aromatics rich stream. The extracted aromatics in the aromatics rich stream may be separated from the solvent through a distillation process and the solvent may be recycled. Suitable solvents that may be used in such a solvent extraction method may include phenol, sulfolane, and N-formyl morpholine. An example of an extractive distillation process is described in U.S. Pat. No. 5,401,365, the disclosure of which is incorporated herein by reference in its entirety.

The raffinate stream in line 114 may comprise the unreacted selectively convertible components and the highly branched hydrocarbons fed to the aromatization reactor system 106, as well as minor amounts of reaction products from the aromatization reactor system 106. In various aspects, the raffinate stream may comprise between about at least about 5 wt. %, 10 wt. %, 20 wt. %, 30 wt. %, 40 wt. %, or 50 wt. % of the highly branched hydrocarbons. The raffinate stream in line 114 may then pass to a highly branched hydrocarbon ("HBH") separation zone 116 that is configured to further separate the highly branched hydrocarbons from the selectively convertible components in the raffinate stream.

Alternatively, molecular sieves may be used to separate product aromatics from the paraffins rich raffinate stream by passing the product stream comprising aromatics and paraffins through a bed of molecular sieves. The molecular sieves tend to adsorb the paraffins, but not the aromatic components.

In order to convert at least a portion of the highly branched hydrocarbons to selectively convertible components in an isomerization reactor system 122, the raffinate stream may be further separated into a stream rich in highly branched hydrocarbons and another stream comprising the selectively convertible components, which may be recycled to the inlet of the aromatization reactor system 106 through recycle stream in line 120 without passing through the isomerization reactor system 122. The raffinate stream may be separated using any suitable separation processes on one or more separation sections within the HBH separation zone 116. In several aspects, a stream rich in highly branched hydrocarbons may be separated from the raffinate stream by distillation in the HBH separation zone 116. The distillation step may be carried out in one or more distillation columns, using conventional distillation techniques conducted in accordance with the removal requirements for the highly branched hydrocarbons present in the raffinate stream. Other suitable separation processes may also be used such as adsorption, membrane separation, or other separation technologies. When the HBH separation zone 116 comprises multiple separation sections, the different separation sections may use the same or different separation processes.

The separation within the HBH separation zone 116 may separate at least about 60 wt. %, at least about 70 wt. %, at least about 80 wt. %, at least about 90 wt. % or at least about 95 wt. % of the highly branched hydrocarbons in the raffinate stream in line 114 into a stream rich in the highly branched hydrocarbons ("HBH Rich Stream") in line 118 passing out of the HBH separation zone 116. In various aspects, the separation within the HBH separation zone 116 may separate at least about 60 wt. %, at least about 70 wt. %, at least about 80 wt. %, at least about 90 wt. % or at least about 95 wt. % of the dimethylbutanes in the raffinate stream in line 114.

The HBH separation zone 116 may result in a recycle stream in line 120 comprising a majority of selectively convertible components with a minor amount of highly branched hydrocarbons and aromatics. In some aspects, the recycle stream in line 120 may comprise less than about 15 wt. %, less than about 10 wt. %, or less than about 8 wt. % highly branched hydrocarbons, based on the total weight of the recycle stream in line 120. The recycle stream may pass back to the inlet of the aromatization reactor system 106. The recycle stream may be combined with the fresh hydrocarbon stream 102 prior to entering the aromatization reactor system 106, and/or pass directly to one or more reactors within the aromatization reaction system 106.

A stream rich in highly branched hydrocarbons may also be produced in the HBH separation zone 116 and pass through line 118 to an isomerization reactor system 122. The concentration of the highly branched hydrocarbons in the stream in line 118 may be greater than about 50 wt. %, greater than about 60 wt. %, greater than about 70 wt. %, or greater than about 80 wt. %, based on the weight of all components in the stream in line 118.

The stream rich in the highly branched hydrocarbons may pass to the isomerization reactor system 122. Additional streams that may comprise highly branched hydrocarbons may also be fed to the isomerization reactor system 122 through one or more lines such as optional line 124. Various processing streams may be used with the present system 100, and streams rich in highly branched hydrocarbons may be fed to the isomerization reactor system 122 as an entry point into the aromatization system 100. This may allow the highly branched hydrocarbons to be isomerized into selectively convertible components prior to entering the aromatization reactor system 106. In some aspects, a feed stream comprising highly branched hydrocarbons may be initially fed to the aromatization system 100 through line 124 in addition to or in place of the fresh hydrocarbon stream 102 to allow the highly branched hydrocarbons to be isomerized prior to passing to the aromatization reactor system 106.

The stream rich in the highly branched hydrocarbons in line 118 and any optional inlet streams in line 124 may pass to the isomerization reactor system 122. The isomerization reactor system 122 may comprise one or more reactors to contact the highly branched hydrocarbons in the stream rich in the highly branched hydrocarbons with an isomerization catalyst under isomerization reaction conditions to form selectively convertible components. While not shown in isomerization reactor system 122, hydrogen may optionally be introduced during the isomerization process. The isomerization reaction may be carried out in one or more reactor vessels within the isomerization reactor system 122 shown in FIG. 1.

In various aspects, the reactor(s) in the isomerization reactor system 122 may contain a catalyst for carrying out an isomerization process. A suitable isomerization catalyst is capable of converting at least a portion of the highly branched hydrocarbons into selectively convertible components. For example, a highly branched hydrocarbon comprising a quaternary carbon atom may be isomerized to a selectively convertible component comprising two tertiary carbon atoms, where the two tertiary carbon atoms are not adjacent to each other. Similarly, a highly branched hydrocarbon comprising two tertiary carbon atoms that are adjacent may be isomerized to a selectively convertible component having two tertiary carbon atoms that are not adjacent, a selectively convertible component having only one tertiary carbon atom (without any quaternary carbon atoms), or a selectively convertible component that does not have any quaternary or tertiary carbon atoms (for example, a normal paraffin). It should be noted that the isomerization of a highly branched hydrocarbon may proceed through another highly branched hydrocarbon before isomerization to a selectively convertible component.

Any catalyst capable of carrying out an isomerization reaction may be used alone or in combination with additional catalytic materials in the reactors. In some aspects, the isomerization catalyst may comprise a platinum alumina catalyst with or without a Friedel-Crafts halide, platinum molecular sieve catalyst, or platinum sulfate metal oxide catalyst. In some aspects, the isomerization catalyst may comprise a chlorided platinum alumina catalyst. The alumina may include an anhydrous gamma-alumina. The catalyst may also contain other platinum group metals. The term platinum group metals refer to noble metals excluding silver and gold selected from the group consisting of platinum, palladium, ruthenium, rhodium, osmium, and iridium. The catalyst may contain from about 0.01 wt. % to about 5 wt. % of the platinum. Other platinum group metals may be present in a concentration of from 0.01 wt. % to about 5 wt. %. The platinum component may exist within the final catalytic composite as an oxide, a halide, or as an elemental metal. The presence of the platinum component in its reduced state has been found most suitable for this process. The chloride component may be present in an amount from about 2 wt. % to about 10 wt. % based upon the dry support material. The inorganic oxide preferably comprises a zeolite (for example, beta zeolite, ZSM-5) and/or alumina, and mixtures thereof. In some aspects, the support may comprise a beta zeolite having a silicon to aluminum molar ratio between about 20 to about 60.

There are a variety of ways for preparing the catalytic composite and incorporating the platinum metal, and optionally, the chloride therein. In one such method, the catalyst is prepared by impregnating the carrier material through contact with an aqueous solution of a water-soluble decomposable compound of the platinum group metal. In various aspects, the isomerization catalyst may comprise a Group X metal. In some aspects, the impregnation is carried out by contacting the carrier material in a solution of tetra amine platinum chloride, potassium hexachloroplatinate, or any combination thereof. Other solutions may comprise chloroplatinic acid, ammonium chloroplatinate, bromoplatinic acid, or platinum dichloride. Use of the platinum chloride compound may incorporate the platinum component and at least a minor quantity of the chloride into the catalyst.

Other suitable isomerization catalyst compositions for use in the present systems and methods may comprise a Group VIII noble metal, a hydrogen form crystalline aluminosilicate, and a refractory inorganic oxide. The Group VIII noble metal may be incorporated into the catalytic composite as described above to supply the hydrogenation-dehydrogenation function. The Group VIII noble metal is present in an amount from about 0.1 to about 5% by weight of the composite. The catalytic composite may also contain a catalytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of the rare earth metals and mixtures thereof. The hydrogen form silica-alumina has either a three-dimensional or channel-pore-structure crystal lattice framework. The three-dimensional aluminosilicates include both synthetic and naturally occurring silica aluminas, such as, the faujasites which include X-type, Y-type, ultrastable-Y and the like. L-type, omega-type, and mordenite are examples of the channel-pore-structure crystalline aluminosilicates. Mordenite in either naturally occurring or synthetic form is preferred, particularly with a silica to alumina molar ratio of at least 16:1.

Operating conditions within the isomerization reactors of the isomerization reactor system 122 are selected to convert the highly branched hydrocarbons to selectively convertible components. In some aspects, temperatures within the isomerization reactors of the isomerization reactor system 122 may range from about 200° C. to about 350° C., or from about 275° C. to about 325° C. Higher reaction temperatures may favor equilibrium mixtures of normal alkanes versus isoalkanes. The isomerization reactor system 122 may be maintained over a wide range of pressures. Pressure conditions in the isomerization reactor system 122 may be between about 50 psig and about 300 psig, or about 75 psig to about 125 psig. The rate of the feed stream (e.g., in the highly branched hydrocarbons stream in line 118 and any optional inlet streams in line 124) to the isomerization reactor or reactors may vary over a wide range. In a number of aspects, the liquid hourly space velocity (LHSV) may range from about 0.5 $hr^{-1}$ to about 10 $hr^{-1}$, or from about 1 $hr^{-1}$ to about 4 $hr^{-1}$, or about 2 $hr^{-1}$.

When hydrogen is introduced as part of the isomerization reaction, the hydrogen may be combined with the inlet stream prior to entering the isomerization reactor system 122, and/or the hydrogen may be introduced prior to one or more isomerization reactors of the isomerization reactor system. The hydrogen may be introduced at a molar ratio of the hydrogen to the highly branched hydrogen of between about 0.1 and about 10, between about 1 and about 5, or at about 2.

An isomerized stream may pass out of the isomerization reactor system 122 through line 126. The conversion of the highly branched hydrocarbons in the isomerization reactor system 122 may be capable of converting at least about 70 wt. %, least about 75 wt. %, or at least about 80 wt. %, (the lowest is about the equilibrium value of 75 wt. % in total, but normally about 80 wt. % with the highest of about 83 wt. %-84 wt. %, during the Time-on-stream test of as long as 100$h$.) of the highly branched hydrocarbons in the inlet streams to the isomerization reactor system 122 to selectively convertible components, based on the total weight of the highly branched hydrocarbons in all of the feed streams to the isomerization reactor system 122. In several aspects of the disclosure, the isomerized stream may comprise between about 5 wt. % and about 50 wt. %, or about 10 wt. % and about 40 wt. %, or about 15 wt. % and about 25 wt. % highly branched hydrocarbons The isomerized stream in line 126 may pass to the inlet of the aromatization reactor system 106. The isomerized stream may be combined with the fresh hydrocarbon stream 102 prior to entering the aromatization reactor system 106 or directly enter one or more reaction sections within the aromatization reactor system 106. Within the aromatization reactor system 106, at least a portion of the selectively convertible components produced in the isomerization reactor system 122 may be converted to aromatic components.

Figure 2:
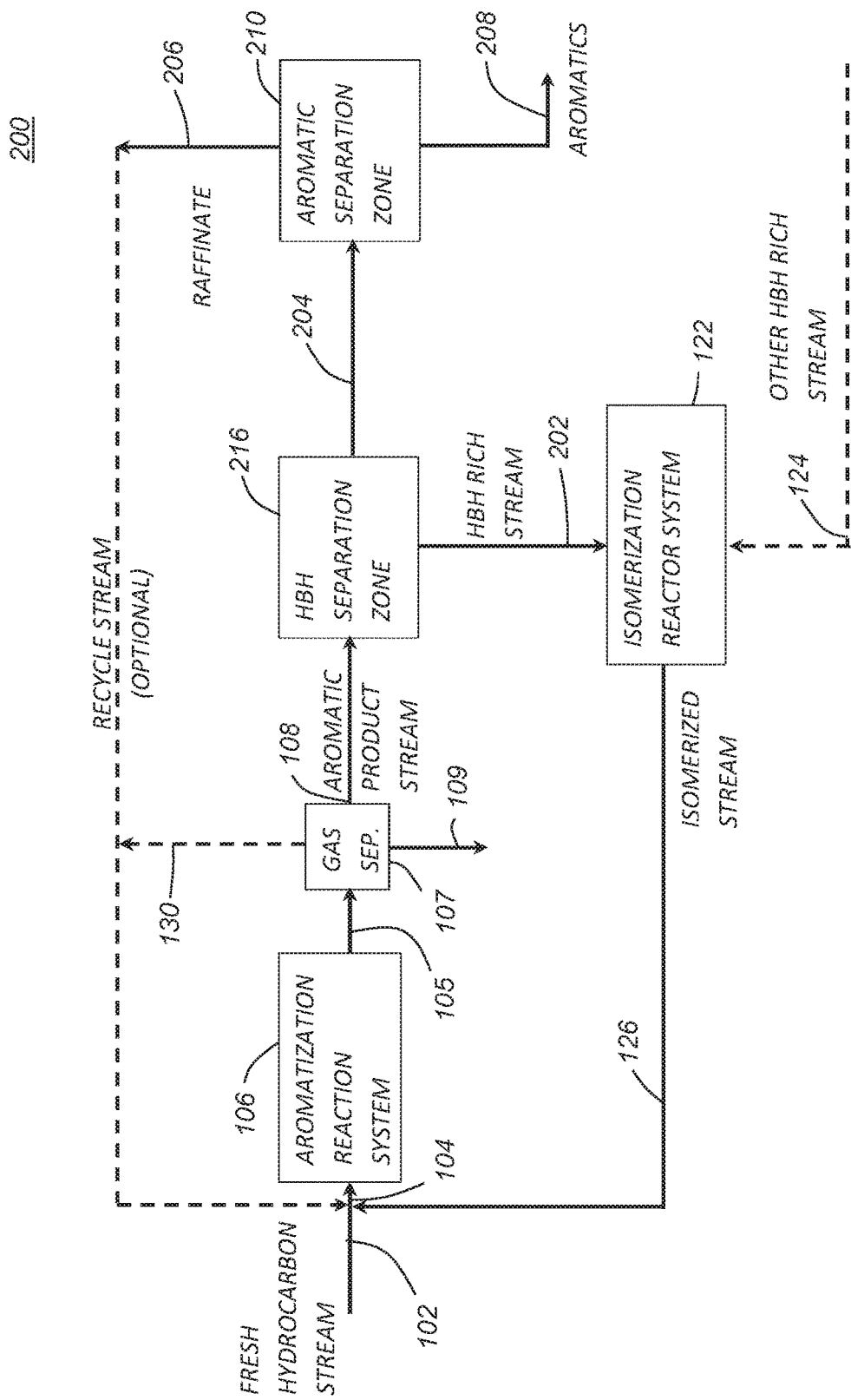
FIG. 2 is another schematic flow diagram of various aspects of an aromatization process of the disclosure.

The aromatization system 100 includes the separation of the aromatic products of the aromatization reaction prior to the separation of the highly branched hydrocarbons from the selectively convertible components. In some aspects, the separation sequence may be reversed to separate the highly branched hydrocarbons from the selectively convertible components and the aromatic product prior to separating the aromatic components from the remaining selectively convertible components and aromatic products. Such an aromatization system 200 for converting the selectively convertible components to aromatic products is illustrated in FIG. 2. The system 200 of FIG. 2 is similar to the aromatization system 100 of FIG. 1, and similar streams and processes or zones will not be described in the interest of brevity. As shown in FIG. 2, the fresh hydrocarbon stream 102 may enter the system 200 and pass to the aromatization reactor system 106. The aromatization product stream in line 108 from the aromatization reactor system 106 may pass to a gas separation zone 107 through line 105, where an optional hydrogen recycle stream can pass through line 130 and a hydrogen product stream can pass through line 109. The remaining aromatic product can pass through line 108 to a HBH separation zone 216 that is configured to process a raw aromatization product and separate the highly branched hydrocarbons from the unreacted selectively convertible components, and the aromatic products. The HBH separation zone 216 may be the same or similar to the HBH separation zone 116 described with respect to FIG. 1, and any of the separation processes described with respect to the HBH separation zone 116 of FIG. 1 may be used in the HBH separation zone 216. The stream rich in the highly branched hydrocarbons, the HBH rich stream, in line 202 may pass to an isomerization reactor system 122, and the stream comprising the unreacted selectively convertible components and aromatic products may pass to an aromatic separation zone 210.

The separation within the HBH separation zone 216 may separate at least about 60 wt. %, at least about 70 wt. %, at least about 80 wt. %, at least about 90 wt. % or at least about 95 wt. % of the highly branched hydrocarbons in the aromatization product stream in line 108 into the stream rich in the highly branched hydrocarbons passing out of the HBH separation zone 216 in line 202. In other aspects of the disclosure, the separation within the HBH separation zone 216 may separate at least about 60 wt. %, at least about 70 wt. %, at least about 80 wt. %, at least about 90 wt. % or at least about 95 wt. % of the dimethylbutanes in the aromatization product stream in line 108. The concentration of the highly branched hydrocarbons in line 202 may be greater than about 50 wt. %, greater than about 60 wt. %, greater than about 70 wt. %, or greater than about 80 wt. %, based on the total weight of all of the components of the stream in line 202.

The stream rich in the highly branched hydrocarbons may pass to an isomerization reactor system 122 that may be the same as or similar to the isomerization reactor system 122 described with respect to FIG. 1. One or more additional streams comprising highly branched hydrocarbons may optionally be provided to the isomerization reactor system 122. The resulting effluent from the isomerization reactor system 122 may pass to the inlet of the aromatization reactor system 106 as described herein.

The stream comprising the unreacted selectively convertible components and aromatic products may pass to an aromatic separation zone 210. The stream in line 204 may predominately comprise one or more selectively convertible components (for example, unreacted selectively convertible components from the aromatization reactor system 106, by-products) and the aromatic product from the aromatization reactor system 106. The aromatic separation zone 210 may separate the stream into a raffinate stream in line 206 and an aromatic stream in line 208. The aromatic separation zone may be the same as or similar to the aromatic separation zone 110 described with respect to FIG. 1, and any of the separation processes described with respect to the aromatic separation zone 110 in FIG. 1 may be used with the aromatic separation section 210.

The resulting raffinate stream in line 206 may be rich in selectively convertible components that may optionally be recycled to the inlet of the aromatization reaction zone 106. The aromatic stream in line 208 may be rich in the aromatic product from the aromatization reactor system 106 and may pass out of the system 200 as a product stream. One or more additional treatment processes may be performed on the aromatic product stream prior to the aromatic product stream leaving the system.

Referring to FIG. 1 and FIG. 2, an aromatization process may be carried out using the aromatization system 100 or 200. In various aspects of the disclosure, a process for aromatizing hydrocarbons may include converting at least a portion of the highly branched hydrocarbons in a feed stream into selectively convertible components. For example, an isomerization reaction may be used to convert the highly branched hydrocarbons into selectively convertible components. The isomerization reaction may be carried out by contacting the feed stream comprising the highly branched hydrocarbons with an isomerization catalyst contained in at least one isomerization reactor within an isomerization reactor system 122 under isomerization reaction conditions. The resulting reaction may isomerize a portion of the highly branched hydrocarbons in the feed stream into the selectively convertible components.

The resulting effluent stream from isomerization reactor system may then pass to an aromatization zone to undergo an aromatization reaction, as described in more detail herein. In various aspects of the disclosure, the selectively convertible components in the isomerized stream in line 126 may contact a dehydrocyclization catalyst in an aromatization reactor system 106 under aromatization reaction conditions to convert the selectively convertible components into one or more aromatic components. The resulting effluent stream may comprise an aromatic product as a result of at least a portion of the selectively convertible components being converted into aromatic components along with unconverted selectively convertible components and some amount of highly branched hydrocarbons.

In some aspects, the aromatization reactor effluent may pass to an HBH separation zone 216 where at least a portion of highly branched hydrocarbons may be separated to obtain a highly branched hydrocarbon stream passing through line 202 that has an increased highly branched hydrocarbon concentration compared to the aromatization reactor effluent. The highly branched hydrocarbon stream may be provided to the isomerization reactor system 122 as the feed stream. The remaining stream passing from the HBH separation zone 216 may pass to an aromatic separation zone 210, where the aromatic product may be separated from the remaining stream. The aromatic product stream passing through line 208 may have an increased aromatic concentration as compared to the stream passing to the aromatic separation section through line 204. A second stream comprising the selectively convertible components in line 206 may also be recovered from the aromatic separation section. The second stream may have an increased selectively convertible component content as compared to the stream passing to the aromatic separation section through line 204, and the second stream may be recycled to the aromatization reaction for further conversion.

In various aspects of the process for aromatizing hydrocarbons, the highly branched hydrocarbons may be recovered from an aromatization reactor effluent, and converting at least a portion of the highly branched hydrocarbons into selectively convertible components. The highly branched hydrocarbons may be converted to selectively convertible components by contacting the highly branched hydrocarbons with an isomerization catalyst contained in at least one isomerization reactor within an isomerization reaction process, and isomerizing at least the portion of the highly branched hydrocarbons into the selectively convertible components.

The resulting stream from the isomerization reactor system may be fed to an inlet of an aromatization reaction process to aromatize the selectively convertible components and produce an aromatic product. The effluent stream from the aromatization process may be separated to obtain an aromatic product stream and a stream enriched in the highly branched hydrocarbons. The stream enriched in the highly branched hydrocarbons may be recycled to the isomerization reactor system to produce selectively convertible components that may be further reacted to form aromatic products.

In still other aspects of the disclosure, selectively convertible components may be converted to aromatic hydrocarbons by concentrating highly branched hydrocarbons in a hydrocarbon stream to yield a highly branched hydrocarbon stream that is enriched in highly branched hydrocarbons. In various aspects, the highly branched hydrocarbons may be concentrated by separating aromatics from the hydrocarbon stream to yield the highly branched hydrocarbon stream. In various aspects, the highly branched hydrocarbons may be concentrated by separating one or more highly branched hydrocarbons from the hydrocarbon stream to yield the highly branched hydrocarbons rich stream.

Once concentrated, at least a portion of the highly branched hydrocarbons in the highly branched hydrocarbon stream may be converted into selectively convertible components. The highly branched hydrocarbons may be converted by contacting the highly branched hydrocarbons with an isomerization catalyst contained in at least one isomerization reactor within an isomerization reactor system, which may convert at least the portion of the highly branched hydrocarbons into the selectively convertible components. The resulting selectively convertible components may then be passed to an aromatization reaction process wherein at least a portion of the selectively convertible components may be converted to aromatic products.

The system and methods described herein allow a dehydrocyclization reaction to proceed using a variety of feed streams, including those comprising highly branched hydrocarbons. The process also reduces the need for difficult separation processes to remove the highly branched hydrocarbons within the system, which may be difficult to separate from the selectively convertible components due to close boiling points. As a result of including the isomerization reactor system, feed streams may be used from a broader range of sources. In some instances, feed streams having a high level of highly branched hydrocarbons may be fed to the isomerized reactor system prior to entering the aromatization reactor system. Thus, the system provided herein may provide an advantage over prior systems that may not process the highly branched hydrocarbons present in the feed stream.

EXAMPLES

The disclosure having been generally described, the following examples are given as particular aspects of the disclosure and to demonstrate the practice and advantages thereof. It is understood that the examples are given by way of illustration and are not intended to limit the specification or the claims in any manner.

In the following examples, the β zeolite samples of the powder form (H-BEA 25, sample No. 11-00534/04, $SiO_2/Al_2O_3$=25) and extrudate form (T4546, 1/16", sample No. 10740-S) were commercially available from Clariant.

Example 1

In a first example, an isomerization catalyst as described herein was prepared and demonstrated. The catalyst was prepared by incipient wetness impregnation method, using 0.0857 g tetra ammine platinum chloride in 8.6 g distilled $H_2O$ solution impregnated on 10 g β zeolite of the powder form. The obtained sample was dried at room temperature for 16 hours, then dried at 120° C. for 2 hours (with a ramping rate of 5° C./min) followed by a calcination at 500° C. for 4 hours (with a ramping rate of 5° C. min).

Figure 3:
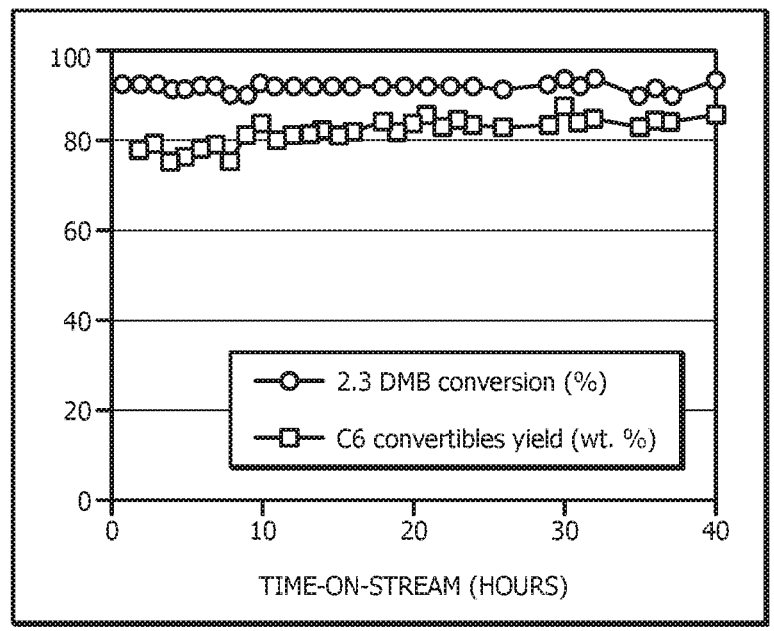
FIG. 3 is a graphical representation of the results of an isomerization using some aspects of a catalyst as described herein.

The typical results showed about an average 91.1% 2,3-dimethylbutane (2,3-DMB) conversion and 81.4% total $C_6$ convertibles yield (including 2-methylpentane, 3-methylpentane, n-hexane, methyl-cyclopentane and cyclohexane) at about 40 hours-on-stream at 100 psig, 300° C., 2 $hr^{-1}$ LHSV and $2H_2$/HC. The results are shown in FIG. 3, which graphically illustrates the 2,3-DMB conversion and $C_6$ convertibles yield over the 0.5% Pt/β-Zeolite catalyst.

Example 2

This example shows another isomerization catalyst. The catalyst was prepared by incipient wetness impregnation method, using 0.1246 g potassium hexachloroplatinate in distilled 8.6 g $H_2O$ solution impregnated on 10 g β zeolite of the powder form. The obtained sample was dried at room temperature for 16 hours, then dried at 120° C. for 2 hours (with a ramping rate of 5° C./min) followed by a calcination at 500° C. for 4 hours (with a ramping rate of 5° C./min).

Figure 4:
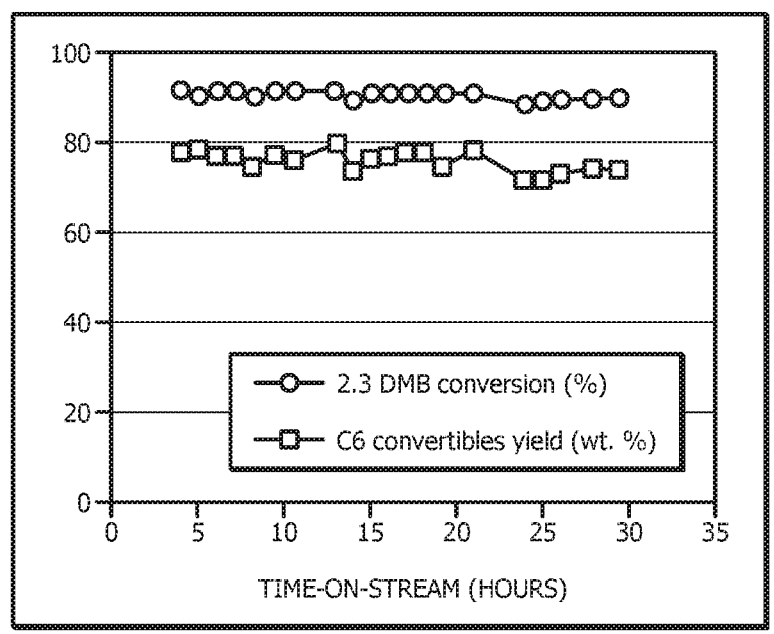
FIG. 4 is another graphical representation of the results of an isomerization using some aspects of a catalyst as described herein.

The typical results showed about an average 90.9% 2,3-DMB conversion and 77.0% total $C_6$ convertibles yield (including 2-methylpentane, 3-methylpentane, n-hexane, methyl-cyclopentane and cyclohexane) at about 40 hours-on-stream at 100 psig, 300° C., 2 $hr^{-1}$ LHSV and $2H_2$/HC. The results are shown in FIG. 4, which graphically illustrates the 2,3-DMB conversion and $C_6$ convertibles yield over the 0.5% Pt/β-Zeolite catalyst.

Example 3

This example shows still another isomerization catalyst. The catalyst was prepared by incipient wetness impregnation method, using 0.1714 g tetra ammine platinum chloride in distilled 12.1 g $H_2O$ solution (PH value modified by ammonia to 6.5-7) impregnated on 20 g β zeolite of the extrudate form. The obtained sample was dried at room temperature for 16 hours, then dried at 120° C. for 2 hours (with a ramping rate of 5° C./min) followed by a calcination at 500° C. for 4 hours (with a ramping rate of 5° C./min).

Figure 5:
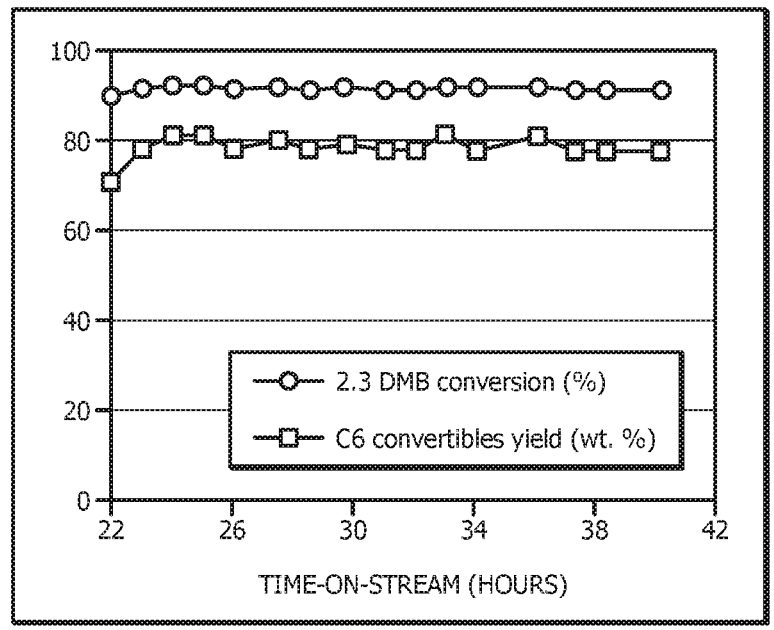
FIG. 5 is still another graphical representation of the results of an isomerization using some aspects of a catalyst as described herein.

The results are shown in FIG. 5, which graphically illustrates the 2,3-DMB conversion and $C_6$ convertibles yield over 0.5% Pt/β-Zeolite catalyst at 100 psig, 300° C., 2 $hr^{-1}$ LHSV and $2H_2$/HC.

Example 4

This example shows another isomerization catalyst. The catalyst was prepared by incipient wetness impregnation method, using 0.2492 g potassium hexachloroplatinate in distilled 12.1 g $H_2O$ solution impregnated on 20 g β zeolite of the extrudate form. The obtained sample was dried at room temperature for 16 hours, then dried at 120° C. for 2 hours (with a ramping rate of 5° C./min) followed by calcination at 500° C. for 4 hours (with a ramping rate of 5° C./min).

Figure 6:
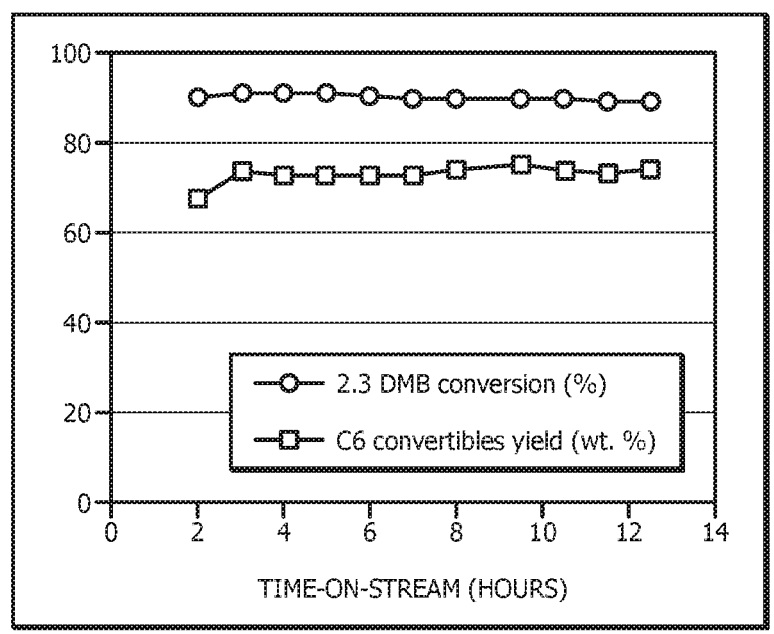
FIG. 6 is yet another graphical representation of the results of an isomerization using some aspects of a catalyst as described herein.

The results are shown in FIG. 6, which graphically illustrates the 2,3-DMB conversion and $C_6$ convertibles yield over 0.5% Pt/β-Zeolite catalyst at 100 psig, 300° C., 2 $hr^{-1}$ LHSV and $2H_2$/HC.

Example 5

This example shows another isomerization catalyst. The catalyst was prepared by incipient wetness impregnation method, using 0.1714 g tetra ammine platinum chloride in 5.6 g distilled $H_2O$ solution impregnated on ZSM-5 zeolite (Si/Al=55) of the powder form. The obtained sample was dried at room temperature for 16 hours, then dried at 120° C. for 2 hours (with a ramping rate of 5° C./min) followed by a calcinations at 500° C. for 4 hours (with a ramping rate of 5° C./min).

Figure 7:
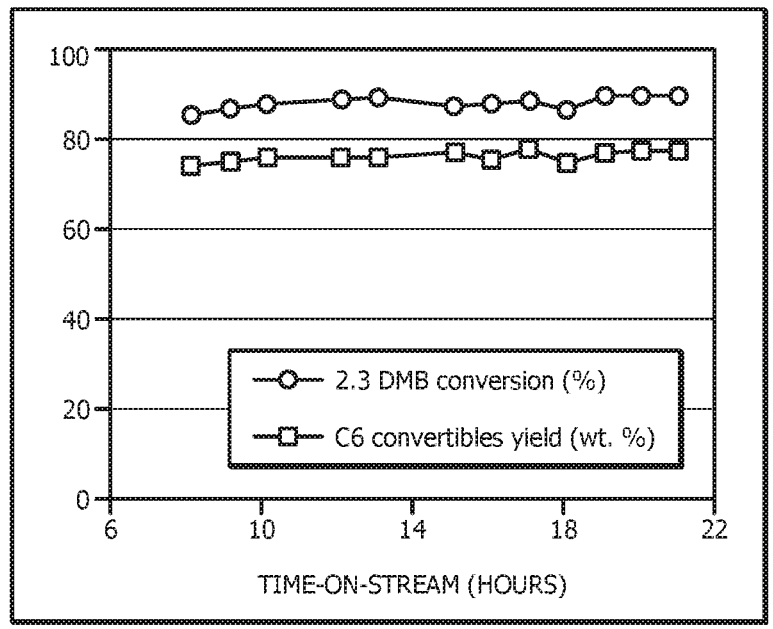
FIG. 7 is another graphical representation of the results of an isomerization using some aspects of a catalyst as described herein.

The results are shown in FIG. 7, which graphically illustrates the 2,3-DMB conversion and $C_6$ convertibles yield over 0.5% Pt/ZSM-5 (Si/AI=55) catalyst at 100 psig, 300° C., 2 LHSC and $2H_2$/HC.

Example 6

This example shows still another isomerization catalyst. The catalyst was prepared by incipient wetness impregnation method, using 0.0853 g tetra ammine platinum chloride in 5.5 g distilled $H_2O$ solution impregnated on 10 g ZSM-5 zeolite (Si/AI=30) of the powder form. The obtained sample was dried at room temperature for 16 hours, then dried at 120° C. for 2 hours (with a ramping rate of 5° C./min) followed by a calcinations at 500° C. for 4 hours (with a ramping rate of 5° C./min).

Figure 8:
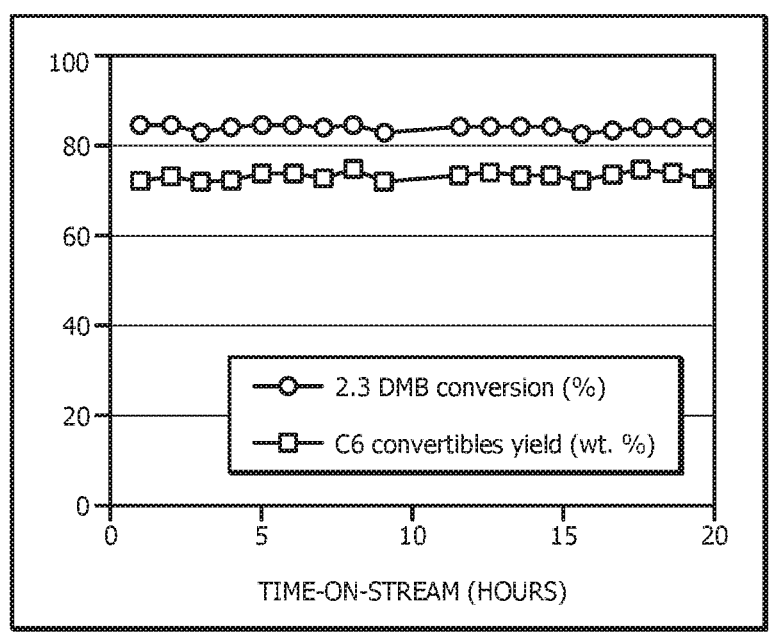
FIG. 8 is still another graphical representation of the results of an isomerization using some aspects of a catalyst as described herein.

The results are shown in FIG. 8, which graphically illustrates the 2,3-DMB conversion and $C_6$ convertibles yield over 0.5% Pt/ZSM-5 (Si/AI=30) catalyst at 100 psig, 293° C., 2 LHSC and $2H_2$/HC.

Additional Embodiments

The following are non-limiting, specific aspects in accordance with the present disclosure:

In a first aspect, a process for aromatizing hydrocarbons comprises: converting at least a portion of highly branched hydrocarbons in a feed stream into convertible components; and aromatizing the selectively convertible components to produce an aromatization reactor effluent, wherein the aromatization reactor effluent comprises an aromatic product.

A second aspect may include the process of the first aspect, wherein converting at least the portion of the highly branched hydrocarbons into the selectively convertible components comprises: contacting the feed stream with an isomerization catalyst in an isomerization reactor within in an isomerization reactor system under isomerization reaction conditions; and isomerizing the portion of the highly branched hydrocarbons in the feed stream into the selectively convertible components.

A third aspect may include the process of the second aspect, wherein the isomerization catalyst comprises a β zeolite.

A fourth aspect may include the process of the third aspect, wherein the isomerization catalyst comprises a Group 10 metal.

A fifth aspect may include the process of the third or fourth aspect, wherein the isomerization catalyst comprises between about 0.1 wt. % and about 1 wt. % platinum on the β zeolite.

A sixth aspect may include the process of any of the third to fifth aspects, wherein a silicon to aluminum molar ratio of the β zeolite is between about 20 to about 60.

A seventh aspect may include the process of any of the first to sixth aspects, wherein the highly branched hydrocarbons comprise hydrocarbons having six or seven carbon atoms with an internal quaternary carbon, or hydrocarbons having six carbon atoms and two adjacent internal tertiary carbons, or mixtures thereof.

An eighth aspect may include the process of the seventh aspect, wherein the highly branched hydrocarbons comprise dimethylbutanes, trimethylbutanes, dimethylpentanes, or mixtures thereof.

A ninth aspect may include the process of the seventh aspect, wherein the highly branched hydrocarbons comprise 2,2-dimethylbutane, 2,3-dimethylbutane, 2,2,3-trimethylbutane 2,2-dimethylpentane, 2,3-dimethylpentane. 2,2-dimethylhexane, 2,3-dimethylhexane, or mixtures thereof.

A tenth aspect may include the process of any of the first to ninth aspects, wherein the selectively convertible components may comprise hydrocarbons having six or seven carbon atoms without an internal quaternary carbon or hydrocarbons having six carbon atoms and without two adjacent internal tertiary carbons, or mixtures thereof.

An eleventh aspect may include the process of any of the first to ninth aspects, wherein the selectively convertible components may comprise methylpentanes, methylhexanes, or mixtures thereof.

A twelfth aspect may include the process of any of the first to ninth aspects, wherein the selectively convertible components may comprise at least one of 2-methylpentane, 3-methylpentane, n-hexane, 2-methylhexane, 3-methylhexane, n-heptane, or mixtures thereof.

A thirteenth aspect may include the process of any of the first to twelfth aspects, wherein the feed stream comprises between about 0.1 wt. % and about 100 wt. % highly branched hydrocarbons.

A fourteenth aspect may include the process of any of the first to thirteenth aspects, wherein aromatizing the selectively convertible components comprises: contacting the selectively convertible components with a dehydrocyclization catalyst in an aromatization reactor system under aromatization reaction conditions; and converting the selectively convertible components into one or more aromatics in the aromatic product.

A fifteenth aspect may include the process of the fourteenth aspect, wherein the dehydrocyclization catalyst comprises at least one Group VIII metal and zeolitic support.

A sixteenth aspect may include the process of the fifteenth aspect, wherein the least one Group VIII metal comprises platinum and the zeolitic support comprises silica bound L-zeolite.

A seventeenth aspect may include the process of the fifteenth or sixteenth aspect, wherein the dehydrocyclization catalyst comprises one or more halogens.

An eighteenth aspect may include the process of any of the first to seventeenth aspects, wherein the aromatization reactor effluent comprises the highly branched hydrocarbons, and wherein the process further comprises: separating at least a portion of the aromatic product from the aromatization reactor effluent to obtain a raffinate stream, wherein the raffinate stream has an increased highly branched hydrocarbon concentration compared to the aromatization reactor effluent; and providing the raffinate stream to the isomerization reactor system as the feed stream.

A nineteenth aspect may include the process of any of the first to seventeenth aspects, wherein the aromatization reactor effluent comprises the highly branched hydrocarbons, wherein the process further comprises: separating at least a portion of the aromatic product from the aromatization reactor effluent to obtain a raffinate stream, wherein the raffinate stream has an increased highly branched hydrocarbon concentration compared to the aromatization reactor effluent; and separating the highly branched hydrocarbons from the raffinate stream to obtain the feed stream to the isomerization reactor system, wherein the feed stream has an increased highly branched hydrocarbon concentration compared to the lean raffinate stream.

A twentieth aspect may include the process of any of the first to seventeenth aspects, wherein the aromatization reactor effluent comprises the highly branched hydrocarbons, and wherein the process further comprises: separating at least a portion of the highly branched hydrocarbons from the aromatization reactor effluent to obtain a highly branched hydrocarbon stream, wherein the highly branched hydrocarbon stream has an increased highly branched hydrocarbon concentration compared to the aromatization reactor effluent; and providing the highly branched hydrocarbon stream to the isomerization reactor system as the feed stream.

In a twenty first aspect, a process for aromatizing hydrocarbons comprises: recovering highly branched hydrocarbons from an aromatization reactor effluent; converting at least a portion of the highly branched hydrocarbons into selectively convertible components; and aromatizing the selectively convertible components to produce an aromatic product.

A twenty second aspect may include the process of the twenty first aspect, further comprising: feeding the selectively convertible components to an inlet of an aromatization reactor system, wherein the aromatization reactor system produces the aromatization reactor effluent.

A twenty third aspect may include the process of the twenty second aspect, wherein aromatizing the selectively convertible components occurs within the aromatization reactor system.

A twenty fourth aspect may include the process of any of the twenty first to twenty third aspects, wherein converting at least the portion of the highly branched hydrocarbons comprises: contacting the highly branched hydrocarbons with an isomerization catalyst; and isomerizing at least the portion of the highly branched hydrocarbons into the selectively convertible components.

A twenty fifth aspect may include the process of the twenty fourth aspect, wherein the isomerization catalyst comprises a $\beta$ zeolite and a Group 10 metal.

A twenty sixth aspect may include the process of any of the twenty first to twenty fifth aspects, wherein the selectively convertible components may comprise at least one of 2-methylpentane, 3-methylpentane, or n-hexane.

In a twenty seventh aspect, a process for aromatizing hydrocarbons comprises: concentrating highly branched hydrocarbons in a hydrocarbon stream to yield a highly branched hydrocarbon rich stream; converting at least a portion of the highly branched hydrocarbons in the highly branched hydrocarbon rich stream into selectively convertible components; and aromatizing the selectively convertible components to produce an aromatization reactor effluent comprising an aromatic product.

A twenty eighth aspect may include the process of the twenty seventh aspect, wherein concentrating the highly branched hydrocarbons comprises separating aromatics from the hydrocarbon stream to yield the highly branched hydrocarbons rich stream.

A twenty ninth aspect may include the process of the twenty seventh or twenty eighth aspect, wherein concentrating the highly branched hydrocarbons comprises separating at least a portion of the highly branched hydrocarbons from the hydrocarbon stream to yield the highly branched hydrocarbons rich stream.

A thirtieth aspect may include the process of any of the twenty seventh to twenty ninth aspects, wherein the hydrocarbon stream is the aromatization reactor effluent.

A thirty first aspect may include the process of any of the twenty seventh to thirtieth aspects, wherein converting at least the portion of the highly branched hydrocarbons into selectively convertible components comprises: contacting the highly branched hydrocarbons with an isomerization catalyst; and isomerizing at least the portion of the highly branched hydrocarbons into the selectively convertible components.

A thirty second aspect may include the process of the thirty first aspect, wherein the isomerization catalyst comprises a $\beta$ zeolite and platinum.

In a thirty third aspect, an aromatization reactor system comprises: at least one aromatization reactor comprising a dehydrocyclization catalyst, a feed inlet, and an aromatization reactor effluent outlet; a separator in fluid communication with the aromatization reactor effluent outlet, wherein the separator is configured to separate at least a portion of an aromatization reactor effluent stream comprising an aromatic product and highly branched hydrocarbons into an aromatic product stream enriched in aromatics and a highly branched hydrocarbon stream enriched in the highly branched hydrocarbons, wherein the separator is configured to pass the highly branched hydrocarbon stream out of a highly branched hydrocarbon stream outlet; and an isomerization reactor system comprising at least one isomerization reactor further comprising an isomerization catalyst, wherein the isomerization reactor system is in fluid communication with the highly branched hydrocarbon stream outlet to receive the highly branched hydrocarbon stream; wherein the isomerization reactor system is configured to isomerize at least a portion of the highly branched hydrocarbons in the highly branched hydrocarbon stream into selectively convertible components, wherein an outlet of the isomerization reactor system is in fluid communication with the feed inlet of the aromatization reactor system to pass at least a portion of the selectively convertible components from the isomerization reactor system to the aromatization reactor system.

A thirty fourth aspect may include the system of the thirty third aspect, wherein the isomerization catalyst comprises a $\beta$ zeolite.

A thirty fifth aspect may include the system of the thirty fourth aspect, wherein a silicon to aluminum molar ratio of the $\beta$ zeolite is between about 20 to about 60.

A thirty sixth aspect may include the system of any of the thirty third to thirty fifth aspects, wherein the isomerization catalyst comprises a Group 10 metal.

A thirty seventh aspect may include the system of any of the thirty third to thirty sixth aspects, wherein the isomerization catalyst comprises between about 0.1 wt. % and about 1 wt. % platinum on the $\beta$ zeolite.

A thirty eighth aspect may include the system of any of the thirty third to thirty seventh aspects, wherein the dehydrocyclization catalyst comprises at least one Group VIII metal and zeolitic support.

A thirty ninth aspect may include the system of the thirty eighth aspect, wherein the least one Group VIII metal comprises platinum and the zeolitic support comprises silica bound L-zeolite.

A fortieth aspect may include the system of the thirty eighth or thirty ninth aspect, wherein the dehydrocyclization catalyst comprises one or more halogens.

While the present disclosure has been illustrated and described in terms of particular apparatus and methods of use, it is apparent that equivalent techniques, components and constituents may be substituted for those shown, and other changes may be made within the scope of the present disclosure as defined by the appended claims.

The particular aspects disclosed herein are illustrative only, as the disclosure may be modified and practiced in different but equivalent manners apparent to those skilled in the art having the benefit of the teachings herein. Furthermore, no limitations are intended to the details of construction or design herein shown, other than as described in the claims below. It is there-fore evident that the particular aspects disclosed above may be altered or modified and all such variations are considered within the scope and spirit of the disclosure. Accordingly, the protection sought herein is as set forth in the claims below.

We claim:

1. A process for aromatizing hydrocarbons comprising:
concentrating highly branched hydrocarbons in a hydrocarbon stream to yield a highly branched hydrocarbon rich stream, wherein the highly branched hydrocarbons comprise hydrocarbons having six or seven carbon atoms with an internal quaternary carbon or hydrocarbons having six carbon atoms and two adjacent internal tertiary carbons, or mixtures thereof;
converting at least a portion of the highly branched hydrocarbons in the highly branched hydrocarbon rich stream into selectively convertible components by contacting the highly branched hydrocarbons with an isomerization catalyst and isomerizing at least the portion of the highly branched hydrocarbons into the selectively convertible components; and
aromatizing the selectively convertible components to produce an aromatization reactor effluent comprising an aromatic product,
wherein the isomerization catalyst comprises a platinum alumina catalyst with or without a Friedel-Crafts halide, platinum molecular sieve catalyst, or platinum sulfate metal oxide catalyst.

2. The process of claim 1, wherein the isomerization catalyst comprises a chlorided platinum alumina catalyst.

3. The process of claim 2, wherein alumina comprises an anhydrous gamma-alumina.

4. The process of claim 2, wherein the chloride component is present in an amount from about 2 wt. % to about 10 wt. % based upon weight of dry support material.

5. The process of claim 1, wherein the isomerization catalyst comprises from about 0.01 wt. % to about 5 wt. % of the platinum.

6. The process of claim 5, wherein the isomerization catalyst further comprises at least one noble metal selected from the group consisting of palladium, ruthenium, rhodium, osmium, and iridium.

7. The process of claim 6, wherein the isomerization catalyst comprises the at least one noble metal in a concentration of from 0.01 wt. % to about 5 wt. %.

8. The process of claim 1, wherein concentrating the highly branched hydrocarbons comprises separating aromatics from the hydrocarbon stream to yield the highly branched hydrocarbon rich stream.

9. The process of claim 1, wherein concentrating the highly branched hydrocarbons comprises separating at least a portion of the highly branched hydrocarbons from the hydrocarbon stream to yield the highly branched hydrocarbon rich stream.

10. The process of claim 1, wherein the hydrocarbon stream is the aromatization reactor effluent and the process comprises separating at least a portion of the aromatic product from the aromatization reactor effluent to obtain a raffinate stream; separating at least a portion of the highly branched hydrocarbons from the raffinate stream to yield the highly branched hydrocarbon rich stream.

11. The process of claim 1, wherein the step of aromatizing is performed in an aromatization reactor system comprising:
at least one aromatization reactor comprising a dehydrocyclization catalyst, a feed inlet, and an aromatization reactor effluent outlet;
a separator in fluid communication with the aromatization reactor effluent outlet, wherein the separator is configured to separate at least a portion of the aromatization reactor effluent comprising the aromatic product and the highly branched hydrocarbons into an aromatic product stream enriched in aromatics and a highly branched hydrocarbon stream enriched in the highly branched hydrocarbons, wherein the separator is configured to pass the highly branched hydrocarbon stream out of a highly branched hydrocarbon stream outlet; and
wherein the step of converting is performed in an isomerization reactor system comprising at least one isomerization reactor comprising the isomerization catalyst, wherein the isomerization reactor system is in fluid communication with the highly branched hydrocarbon stream outlet to receive the highly branched hydrocarbon stream;
wherein the isomerization reactor system is configured to isomerize at least a portion of the highly branched hydrocarbons in the highly branched hydrocarbon stream into selectively convertible components, wherein an outlet of the isomerization reactor system is in fluid communication with the feed inlet of the aromatization reactor system to pass at least a portion of the selectively convertible components from the isomerization reactor system to the aromatization reactor system.

12. The process of claim 11, wherein the isomerization catalyst comprises a β zeolite.

13. The process of claim 12, wherein the isomerization catalyst comprises between about 0.1 wt. % and about 1 wt. % platinum on the β zeolite.

14. The process of claim 11, wherein the dehydrocyclization catalyst comprises at least one Group VIII metal and zeolitic support.

15. The process of claim 14, wherein the least one Group VIII metal comprises platinum; the zeolitic support comprises silica bound L-zeolite; and the dehydrocyclization catalyst further comprises one or more halogens.

16. The process of claim 11, wherein the separator is further configured to concentrate the highly branched hydrocarbon stream to yield the highly branched hydrocarbon rich stream and then to pass the highly branched hydrocarbon rich stream out of the highly branched hydrocarbon stream outlet.

* * * * *